US012805816B2

(12) United States Patent
Nyholm et al.

(10) Patent No.: US 12,805,816 B2
(45) Date of Patent: Nov. 24, 2026

(54) CT IMAGING APPARATUS AND CABLING ARRANGEMENT

(71) Applicant: Planmeca Oy, Helsinki (FI)

(72) Inventors: Kustaa Nyholm, Helsinki (FI); Christian De Godzinsky, Helsinki (FI); Tommi Syrjälä, Helsinki (FI)

(73) Assignee: Planmeca Oy, Helsinki (FI)

( * ) Notice: Subject to any disclaimer, the term of this patent is extended or adjusted under 35 U.S.C. 154(b) by 433 days.

(21) Appl. No.: 18/289,450

(22) PCT Filed: May 6, 2022

(86) PCT No.: PCT/FI2022/050306
§ 371 (c)(1),
(2) Date: Nov. 3, 2023

(87) PCT Pub. No.: WO2022/234195
PCT Pub. Date: Nov. 10, 2022

(65) Prior Publication Data
US 2024/0252125 A1 Aug. 1, 2024

(30) Foreign Application Priority Data
May 6, 2021 (FI) ..................................... 20210027

(51) Int. Cl.
*A61B 6/03* (2006.01)
*A61B 6/00* (2024.01)
(Continued)

(52) U.S. Cl.
CPC ............ *A61B 6/035* (2013.01); *A61B 6/4085* (2013.01); *A61B 6/4275* (2013.01);
(Continued)

(58) Field of Classification Search
CPC ..... A61B 6/035; A61B 6/0407; A61B 6/4085; A61B 6/4275; A61B 6/4441;
(Continued)

(56) References Cited

U.S. PATENT DOCUMENTS 4,343,996 A 8/1982 Kuipers
4,366,577 A 12/1982 Brandt
(Continued)

FOREIGN PATENT DOCUMENTS

EP 3646793 A2 5/2020
FR 2426005 A1 12/1979
(Continued)

OTHER PUBLICATIONS

Search Report for Finnish Patent No. 20210027, dated Dec. 31, 2021, 2 pages.
(Continued)

*Primary Examiner* — Mark R Gaworecki
(74) *Attorney, Agent, or Firm* — Lippes Mathias LLP

(57) ABSTRACT

The invention relates, in particular, to structures of dental and medical cone beam computed tomography imaging (CBCT) apparatus. The apparatus includes a cabling arrangement which comprises a roller cylinder assembly (123') arranged between an inner (122) and outer cabling support structure (121). The cabling (124) enters and exits this construction and is arranged inside thereof to form a partial loop around a roller cylinder (123) of the roller cylinder assembly (123').

21 Claims, 9 Drawing Sheets

(51) Int. Cl.

| | |
|---|---|
| ***A61B 6/04*** | (2006.01) |
| ***A61B 6/40*** | (2024.01) |
| ***A61B 6/42*** | (2024.01) |
| ***A61B 6/51*** | (2024.01) |
| ***H02G 11/00*** | (2006.01) |
| ***H02G 11/02*** | (2006.01) |
| ***H05G 1/02*** | (2006.01) |

(52) U.S. Cl.
CPC .............. *A61B 6/4441* (2013.01); *A61B 6/51* (2024.01); *A61B 6/56* (2013.01); *H02G 11/00* (2013.01); *H02G 11/006* (2013.01); *H02G 11/02* (2013.01); *H05G 1/02* (2013.01); *A61B 6/0407* (2013.01); *A61B 6/4447* (2013.01); *A61B 6/54* (2013.01)

(58) Field of Classification Search
CPC ........... A61B 6/4447; A61B 6/51; A61B 6/54; A61B 6/56; H02G 11/00; H02G 11/006; H02G 11/02; H05G 1/02
See application file for complete search history.

(56) References Cited

U.S. PATENT DOCUMENTS

| | | | |
|---|---|---|---|
| 4,646,333 | A | 2/1987 | Yoshida |
| 2010/0067649 | A1 | 3/2010 | Noordhoek |
| 2014/0275953 | A1 | 9/2014 | Gregerson |
| 2017/0215825 | A1 | 8/2017 | Johnson |
| 2017/0319151 | A1 | 11/2017 | Listzenberger et al. |

FOREIGN PATENT DOCUMENTS

| | | | | |
|---|---|---|---|---|
| GB | 1308550 | A | | 2/1973 |
| GB | 2022356 | A | | 12/1979 |
| JP | S54019197 | A | | 2/1979 |
| JP | 2002034960 | A | * | 2/2002 |
| WO | 2020245501 | A1 | | 12/2020 |

OTHER PUBLICATIONS

International Search Report for PCT/FI2022/050306, dated Aug. 19, 2022, 4 pages.

* cited by examiner

CT IMAGING APPARATUS AND CABLING ARRANGEMENT

FIELD OF THE INVENTION

The invention relates to computed tomography imaging apparatus. In particular, features of an apparatus according to the invention are applicable for use in the context of dental and medical cone beam computed tomography (CBCT) imaging apparatus.

BACKGROUND OF THE INVENTION

Computed tomography (CT) is a kind of X-ray imaging in which a volume to be imaged is irradiated from different directions and, from the image information thus acquired, a desired two- or three-dimensional image can be reconstructed.

While images need to be acquired from different directions, unless moving an object to be imaged in relation to the imaging apparatus, there is a need to move the imaging means (x-ray source, image detector) about an imaging station of the apparatus whereto the object to be imaged is designed to be positioned. In many imaging modes this calls for rotation over an angular range of 360 degrees while in some instances it is enough to use a range of the order of 180 degrees. In any case, this requirement brings along the problem of how to provide for such components of the apparatus, which move in relation to other components of the apparatus, the power and/or control needed for their operation, or e.g. how to transfer data therefrom.

Prior art includes various ideas and implemented solutions to convey power and/or data under such circumstances and, when using cables, solutions to address the problem of how to physically arrange the cabling in the apparatus so as to be able to adapt to the different mutual spatial operational positions of components. As typical to technical solutions, such prior art solutions have their pros and cons, which may also vary depending on from which point of view one considers the matter.

BRIEF DESCRIPTION OF THE INVENTION

The current invention concerns arranging in a novel way a cabling to components of, especially, a CBCT apparatus, which are arranged to rotate about a rotation axis. In a CBCT apparatus, rotation of imaging means is typically arranged to be possible for at least over 180 degrees. The characteristic features of the invention are defined in the attached claims.

BRIEF DESCRIPTION OF THE FIGURES

The invention is now described in more detail in reference to some of its preferable embodiments and to the attached drawings, of which.

DETAILED DESCRIPTION OF THE INVENTION

Figure 1:
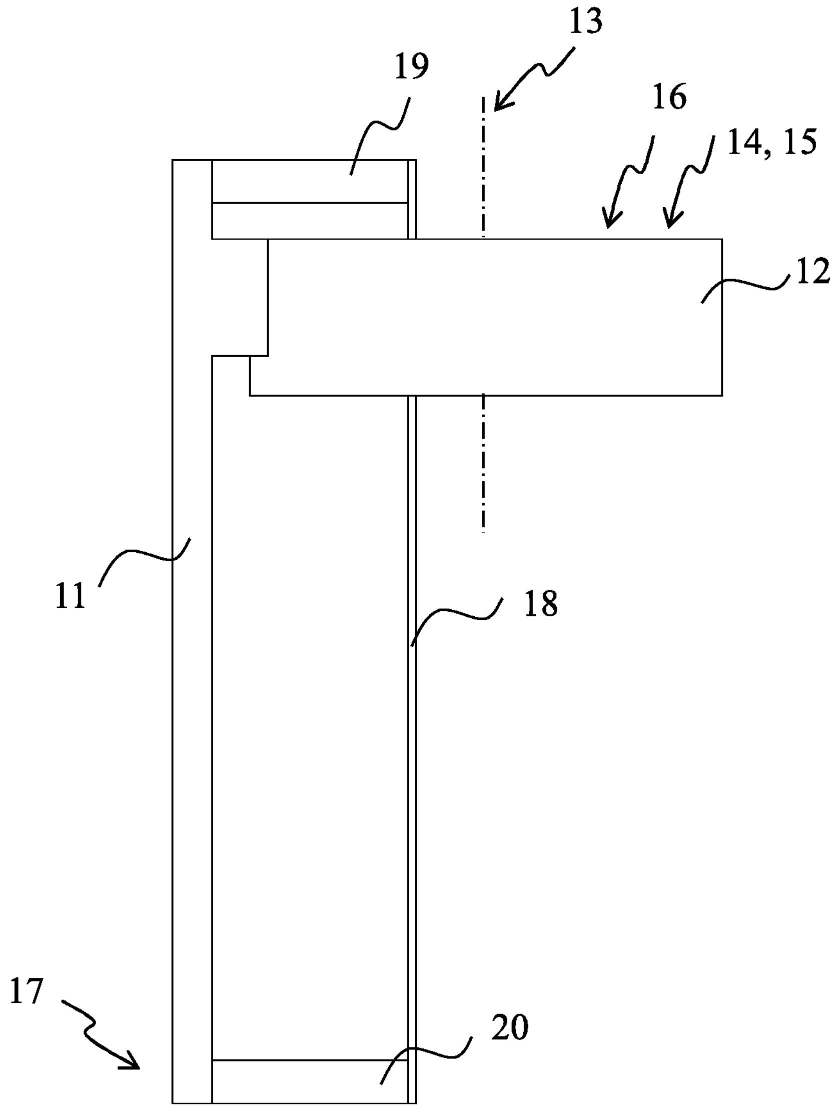
FIG. 1 is a schematic general side view showing certain components, as an example, of one kind of apparatus in which a cabling structure of this disclosure can be implemented.

A more complete understanding of components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms may be used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms “a,” “an,” and “the” include plural referents unless the context clearly dictates otherwise.

As used herein, terms such as about, generally and substantially are intended to encompass structural or numerical modifications which do not significantly affect the purpose of the element or number modified by such term. For example, the term substantially may include a range of variance such as 25%, or 10%, or 0% from the stated relationship.

As used in the specification and in the claims, the term “comprising” may include the embodiments “consisting of” and “consisting essentially of.” The terms “comprise(s),” “include(s),” “having,” “has,” “can,” “contain(s),” and variants thereof, as used herein, are intended to be open-ended transitional phrases, terms, or words that require the presence of the named elements/steps and permit the presence of other elements/steps.

FIG. 1 shows a schematic general side view of certain components of one embodiment, as an example, of an apparatus applicable to comprise the cabling arrangement of this disclosure. The dental or medical CT imaging apparatus of FIG. 1 comprises an elongated frame part 11 extending in a first direction and having a first end and a second end. From this elongated frame part 11 extends in a second direction, which is substantially orthogonal to the first direction, a support construction 12 which supports an X-ray source 14 and an image detector 15 yet which as such are not visible in FIG. 1. The X-ray source 14 and the image detector 15, which together form X-ray imaging means 14, 15, may be mounted to the support construction 12 essentially opposite to each other yet in embodiments, their mutual position may also be arranged to be adjustable.

FIG. 1 further shows a patient support 18 which is a structure mechanically connected to the elongated frame part 11 and extending substantially in parallel with the elongated frame part 11. In the embodiment of FIG. 1, the patient support 18 is essentially of the same length as the elongated frame part 11.

According to one aspect, for example, the length of the elongated frame part 11 is of the order of 240 cm.

According one aspect, for example, the length of the elongated frame part 11 is between 220 cm and 260 cm.

According one aspect, for example, the length of the patient support 18 is 80-90% of the length of elongated frame part 11.

According to one aspect, for example, the patient support 18 has a longer dimension in a first direction and a shorter dimension in a second direction orthogonal to the first direction.

According to one aspect, for example, the patient support 18 is at least in the first direction at least for its prevailing part radiolucent.

According to one aspect, for example, the radiolucent part of the patient support 18 is of essentially the same length as the elongated frame part 11.

According to one aspect, for example, the patient support 18 comprises at least at either of its ends in the first direction a section which is not radiolucent.

According one aspect, for example, the length of the radiolucent part of the patient support 18 in the first direction is 80-90% of the length of the elongated frame part 11.

According to one aspect, for example, the support construction 12 supporting the X-ray imaging means 14, 15 is a circular gantry having a central axis. A gantry housing may partially encircle or completely house the X-ray imaging means 14, 15.

According to one aspect not directly visible in FIG. 1, for example, the apparatus comprises a driving mechanism 16 arranged to drive the X-ray imaging means 14, 15 about a rotation axis. This rotation axis may coincide with the central axis 13 of the support construction 12, which may be in form of a circular gantry, and the central axis may be a physical axis or a virtual rotation axis, like in the case of the structure of FIG. 1.

According to one aspect, for example, the central axis 13 of the gantry coincides the center of rotation/the rotation axis of the X-ray imaging means 14, 15 when they are driven along a curved path.

According to one aspect, the rotation axis is an instantaneous and optionally a virtual rotation axis and the location of the rotation axis in relation to the central axis 13 can be arranged to be changed.

According to one aspect, at least either of the components the ray source 14 and the image detector 15 is arranged to be laterally movable from a location exactly opposite to the other component.

According to one aspect, the structure 12 supporting the X-ray imaging means 14, 15 comprises a gantry having a central axis and the structures of apparatus allows for at least either of: laterally moving the X-ray source 14 between positions at which a central ray it generates coincides with the central axis of the gantry and a position at which the central ray it generates does not coincide with the central axis of the gantry; laterally moving the image detector 15 between positions at which a vector which is normal to the detector surface at the center of the image detector 15 coincides the central axis of the gantry and a position at which the vector which is normal to the detector surface at the center of the image detector 15 does not coincide the central axis of the gantry. The lateral moving of the X-ray imaging means 14, 15 may include moving the X-ray imaging means 14, 15 to a position at which they face each other while the central ray the X-ray source 14 generates does not coincide the central axis of the gantry and the vector which is normal to the detector surface at the center of the image detector 15 does not coincide the central axis of the gantry.

According to another aspect, another driving mechanism 17 is arranged to the apparatus to enable moving the support construction 12 back and forth in a direction which is substantially parallel with the direction in which the elongated frame part 11 extends. According to one aspect, that driving mechanism 17 may be arranged to move the support construction 12 along or alongside the elongated frame part 11.

Figure 2A:
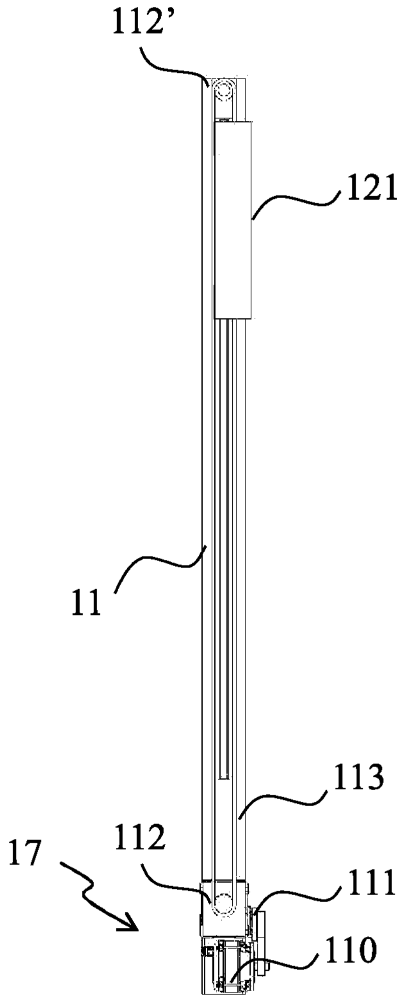
FIGS. 2*a* and 2*b* show structural details applicable for use in the context of an elongated frame part of the apparatus of FIG. 1.
Figure 2B:
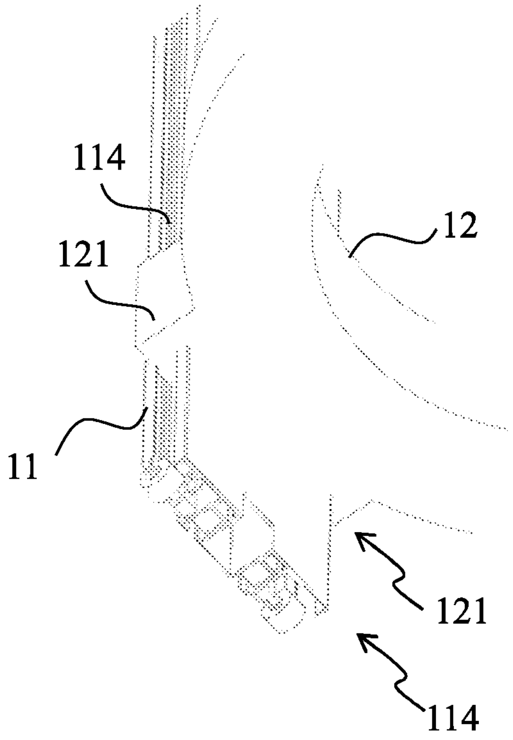

In the example according to FIG. 2*a*, the driving mechanism 17 of the support construction 12 as discussed above comprises a motor 110 and a gearing 111 arranged to rotate a pulley 112. In the construction shown as one embodiment in FIG. 2*a*, while the motor 110 and the pulley 112 are located at the proximity of the second end of the elongated frame part 11 there is also another pulley 112' at the proximity of the first end of the elongated frame part 11 and around the pulleys 112, 112' goes a belt 113, or a correspondingly functioning component like a chain. This mechanism is then functionally connected to the support construction 12 to drive it along the elongated frame part 11, such as shown as an example in FIG. 2*b* where grooves 114 are arranged to the elongated frame part 11 and, to the support construction 12, projecting parts 121 which are fitted to slide along the grooves 114. In an embodiment, to minimize friction, roller type linear guide ways are used in which case the motion is rather rolling than sliding.

According to one aspect not shown in any of the FIGS, for example, the driving mechanism to drive the support construction 12 comprises a motor arranged to the support construction 12 itself.

Regardless of the details of the construction of the driving mechanism 17 to drive the support construction 12 along or alongside the elongated frame part 11, in one embodiment the construction of the apparatus allows for driving the support construction 12 essentially the whole length between the first and second ends of the elongated frame part 11.

According to yet another aspect and as shown is FIG. 1, the apparatus comprises a connection construction 19, 20 which connects the patient support 18 to the elongated frame part 11.

Figure 3:
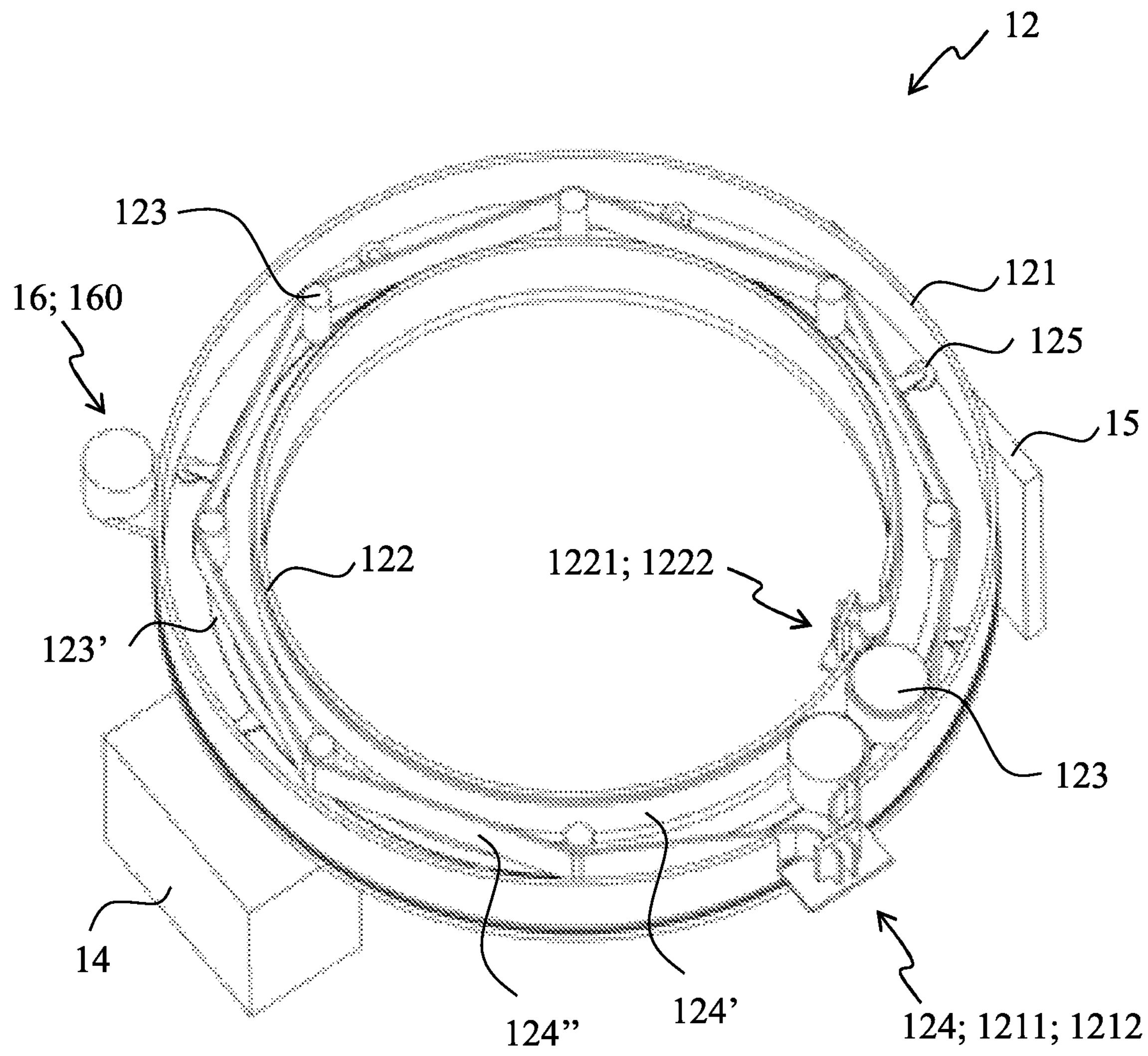
FIG. 3 shows, as an example, some structural details relating to implementing a cabling system according to this disclosure.

FIG. 3 shows, as one example, some structural details relating to implementing a cabling system according to this disclosure. The construction of FIG. 3 comprises as main structures an inner cabling support structure 122 having an outer surface and a virtual central axis 13 (not drawn in FIG. 3), a roller cylinder assembly 123' arranged outside the inner cabling support structure 122 and comprising at least a first roller cylinder 123 (in the embodiment of FIG. 3 there is shown a set of roller cylinders 123 out of which two may be considered primary ones and have a larger diameter than the rest), and an outer cabling support structure 121 arranged outside the roller cylinder assembly 123'.

The roller cylinder assembly 123' of the FIG. 3 embodiment comprises a construction of a set of guide wheels 125 dimensioned to be in contact with the inner surface of the outer cabling support structure 121.

The outer and inner cabling support structures 121, 122 of FIG. 3 comprise an entry location 1211 and an exit location 1221 for two, a first and a second section 124', 124" of a cabling 124, at both of which locations there are cable fixing structures 1212, 1222 for the first and second cable section 124',124".

Between its fixing structures, in the case of FIG. 3 embodiment, the first section 124' of the cabling 124 makes a partial loop around a roller cylinder 123, which cylinder can be characterized as a primary roller cylinder 123 for the first section 124' of the cabling 124. Likewise, the second section 124" of the cabling 124 makes a partial loop around another roller cylinder 123, which cylinder can be characterized as a primary roller cylinder 123 for the second section 124" of the cabling 124.

Either of the first and second section 124',124" of the cabling 124 may be, instead of a cable conveying power and/or data, merely an elongated flexible component, such as a rope-like or a chain-like component.

The imaging means 14, 15 are shown in the construction of FIG. 3 just schematically, for the clarity of the FIG. and also in view of that various embodiments allow for mounting them to either of the inner and the outer cabling support structure 121, 122, for example. Still, naming and positioning of the cabling entry and exit locations 1211, 1221 in FIG. 3 is based on an idea that the X-ray imaging means 14, 15 are mounted to the inner cabling support structure 122 so that the cabling 124 enters the FIG. 3 structure from the outside and is led to at least either of the X-ray source 14 and the image detector 15 from the inner, exit location.

Depending on to which of the inner and outer cabling support structure 121, 122 the imaging means 14, 15 are mounted, that cabling support structure may be arranged to be rotatable. FIG. 3 shows a rotation drive construction 160 which may be the driving mechanism 16 as referred to when discussing FIG. 1 above, so in the case of FIG. 3 the driving mechanism 16 can be considered to be arranged to rotate the inner cabling support structure 122. Also the roller cylinder assembly 123' is rotatable—as will be discussed in more detail further below.

Figure 4A:
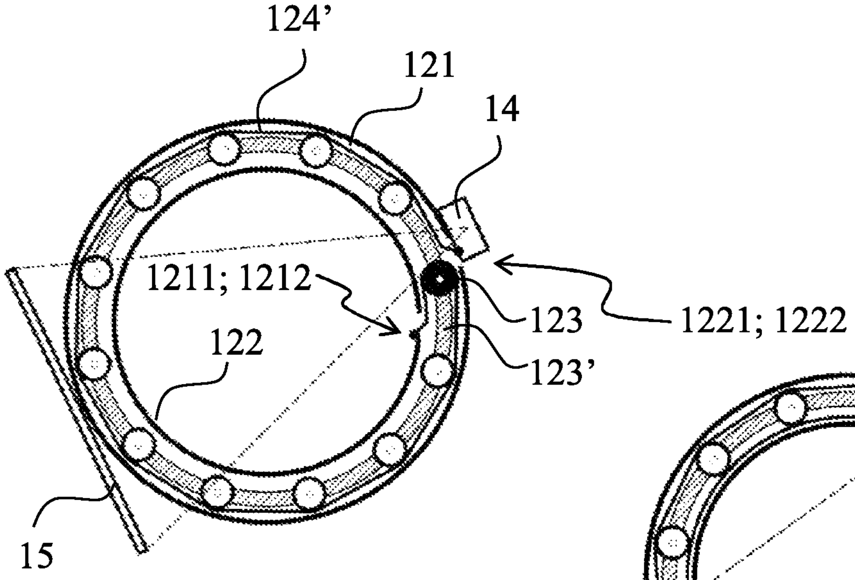
FIGS. 4*a*-4*d* show, as one example, a schematic representation of another structure of the cabling system, at a few of its operational positions.

FIG. 4*a* shows to a certain extent similar embodiment as FIG. 3, in a bit less detail, yet in FIGS. 4*a*-4*d* there is a basic difference in that the component which is arranged to be rotated by the rotation drive construction is the roller cylinder assembly 123'. Another component that is arranged rotatable is the outer cabling support structure 121. Further, FIGS. 4*a*-4*d* show only one cabling section 124' between the entry and exit locations 1211, 1221, the entry location 1211 now being not at the outer but at the inner cabling support structure 122, and the X-ray source 14 and image detector 15 are mounted not to the inner but to the outer cabling support structure 121.

Figure 4C:
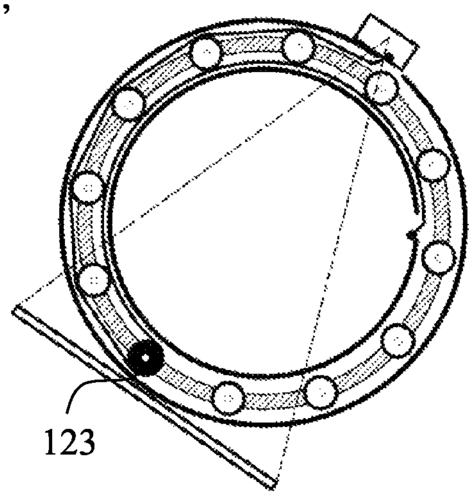
Figure 4B:
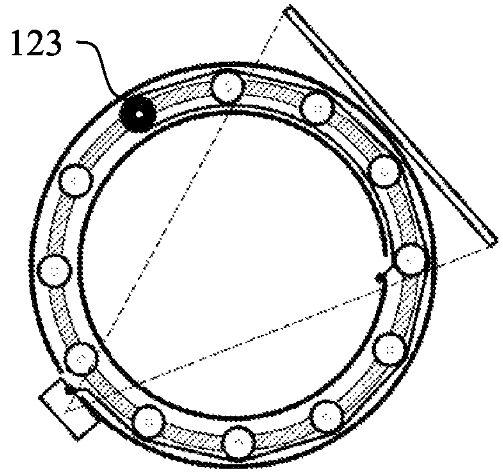
Figure 4D:
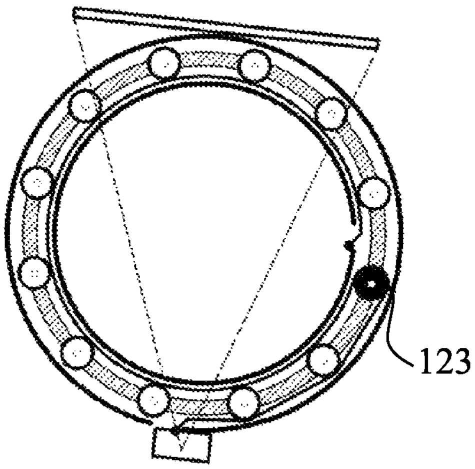

FIGS. 4*a*-4*d* as a combination show the operation principle of the FIG. 4*a* construction. For the clarity of presenting the operation, FIG. 4*b*-4*d* are provided with less reference numbers than FIG. 4*a:*

When the roller cylinder assembly 123' starts to rotate in a counter clock-wise direction and as the cable section 124' makes a partial loop around the primary roller cylinder 123, from the front side of it in relation to the direction of rotation of roller cylinder assembly 123', the primary roller cylinder 123 while starting to move in the counter clock-wise direction i) pulls via the cable section 124' the outer cabling support structure 121 at its cable fixing structure 1222 and ii) also starts to rotate about itself and to roll, bit by bit, the cable section 124' on the outer surface of the inner cabling support structure 122. As a consequence, the roller cylinder assembly 123' will move in the counter clock-wise direction at about half of the velocity of that of the outer cabling support structure 121. Half the velocity means half the distance, within a given time frame, hence e.g. in FIG. 4*b* while the primary roller cylinder 123 has moved somewhat more than 90 degrees, the X-ray source 14 and the image detector 15 mounted to the outer cabling support structure 121 have moved more than 180 degrees. Going further to FIG. 4*c* and finally to FIG. 4*d* one notices that by a slightly less than a full circle rotation of the roller cylinder assembly 123' (FIG. 4*a*→4*d* do not present quite such extreme rotational positions of the primary cylinder) one could generate rotation of the X-ray imaging means 14, 15 of close to two full 360 degree circles, and have at all times the cable section 124' neatly and in a controlled manner tightly arranged within the cabling support structure as a whole.

While FIGS. 4*a*-4*d* show an operation principle of one embodiment according to this disclosure, it does not show a construction by which to generate rotation of the system in an opposite, clockwise direction.

According to one aspect, then, such counter movement may be generated by arranging to the structure another cable section 124", or an elongated flexible component 124", according to the same principles as in the FIG. 4*a* construction but to have that partial loop run from the opposite side of another primary roller cylinder 123 than in the case of FIGS. 4*a*-4*d*. It would also be possible to use the same primary roller cylinder, i.e. to arrange both partial loops around the same roller cylinder 123. By implementing such construction, the system could operate just like discussed above in reference to FIGS. 4*a*-4*d* also in the clockwise direction.

Going back to FIG. 3, now in view of what has been discussed above concerning movement in both clockwise and opposite directions, it is apparent that the FIG. 3 construction enables both of those but, as a consequence of the rotation drive construction being arranged to rotate not the roller cylinder assembly 123' but the inner cabling support construction 122, the partial loop around the primary roller cylinder 123 needs to be arranged around the back side of the first roller cylinder 123, in relation to direction of rotation of the inner cabling support structure 122.

In the FIG. 3 construction, then, when the inner cabling support construction 122 starts to rotate in a first direction, it starts to pull that of the roller cylinders 123 around which the cabling section or the flexible element 124',124" makes the partial loop, from the side opposite to the first direction and, as consequence of that roller cylinder 123 then also starting to rotate, the roller cylinder assembly 123' follows the movement of the inner cabling support construction 122 at about half of the velocity of that of the inner cabling support construction 122. Hence, again, the inner cabling support construction 122 and thus also the imaging means 14, 15 may rotate almost two full circles while the primary roller cylinder 123 moves close to 360 degrees. One way of putting this is that by having a cable section 124' extending e.g. about only one loop inside the FIG. 3 structure, one is still able to rotate the imaging means close to two full 360 degrees rotations.

In yet another embodiment, not shown in the FIGS, the cabling construction is configured such that a rotation drive construction generates rotation of the outer cabling support structure 121 while the inner one is arranged stationary, and the imaging means 14, 15 are mounted to the outer cabling support structure 121. As pointed out, while FIG. 3 does not show details concerning whereto the imaging means 14, 15 are mounted and which component the rotation drive construction is arranged to rotate, one could consider FIG. 3 showing this kind of embodiment as well: This embodiment would operate like discussed above concerning FIG. 3 with the exception that instead of the inner, the outer cabling support construction 121 would be pulling the cabling section or the flexible element 124',124".

In reference to the embodiment and its operational position as shown in FIG. 3, while at the beginning of rotation of the inner cabling support construction 122 in counter clockwise direction, the cabling section 124" fixed at the exit location 1221 pulls the roller cylinder assembly 123' via the primary upper roller cylinder 123 and while that primary roller cylinder 123 rotates and the roller cylinder assembly 123' moves during a given time period a shorter distance than the inner cabling support construction 122, the cabling section 124" keeps on winding on the outer surface of the inner cabling support construction 122. As a consequence, when direction of rotation of the inner cabling support construction 122 is changed and there is no longer a pulling force acting on the cabling section 124" at the exit location 1221 but rather a pushing force, the cabling section 124" being neatly spread on the outer surface of the inner cabling support construction 122 will not bend or get wrinkled when winding off therefrom, due to the primary roller cylinder 123 when now moving in the opposite direction and rotating in the opposite direction about itself keeping on drawing the cabling section 124", also fixed at the entry location 1211, around itself while now moving in the clockwise direction.

It is apparent from the discussion above concerning the FIG. 3 construction that two similarly configured cabling arrangements can be used to enable rotation in both clockwise and counter clock-wise direction.

When having two physically separate cabling sections 124',124", one is able to arrange e.g. another to be a power cable and another a data transfer cable.

According to one aspect, at least either of the cabling sections 124',124" is a flat cable. When using two such cables instead of one which would be wider, one is able to design the whole construction with smaller dimensions in the direction of the width of the flat cable.

While rotation of the roller cylinder assembly 123' in the FIG. 3 embodiment is arranged to take place by using two cable sections generating movement in opposite direction, according to one aspect only one cable section like shown in FIG. 4*a* is used and rotation in the opposite direction is generated by using some other applicable construction, like one operating on spring force.

In embodiments, the shape of the outer surface of the inner cabling support structure 122 is not necessarily a circle as it is shown e.g. in the FIG. 3 construction.

A preferable number of roller cylinders 123 to be used in the construction may depend on various factors. It is preferable, still, to have that many roller cylinders that when the cable section 124 runs outside the surface of the roller cylinders, between two individual adjacent roller cylinders 123, it does not touch the surface of the inner cabling support structure 122.

In case a range of rotation of the imaging means 14, 15 needs not to be as large as the embodiments of FIGS. 3 and 4 make possible, correspondingly shorter cable sections to extend from the entry location to the exit location may be used. And on the other hand, more than one roller cylinder assembly 123' may be used to function in series and thus allow for even larger range of rotation than close to the two full circles as discussed above, in one direction.

According to one aspect, a surface of a roller cylinder comprises protruding edges or another shape designed to prevent the cabling section or the elongated flexible component 124',124" falling off therefrom.

In FIG. 3 all the cable fixing structures 1212, 1222 are shown at a close proximity of the entry and exit locations 1211, 1221 but that does not need to be the case—an end of a cable section 124',124" may be fixed to be immovable in relation to the inner/outer cabling support structure also elsewhere.

Embodiments as discussed above may provide, for one, a stable cabling structure when applied in constructions where the direction in which the gravity field affects them may change.

Figure 5:
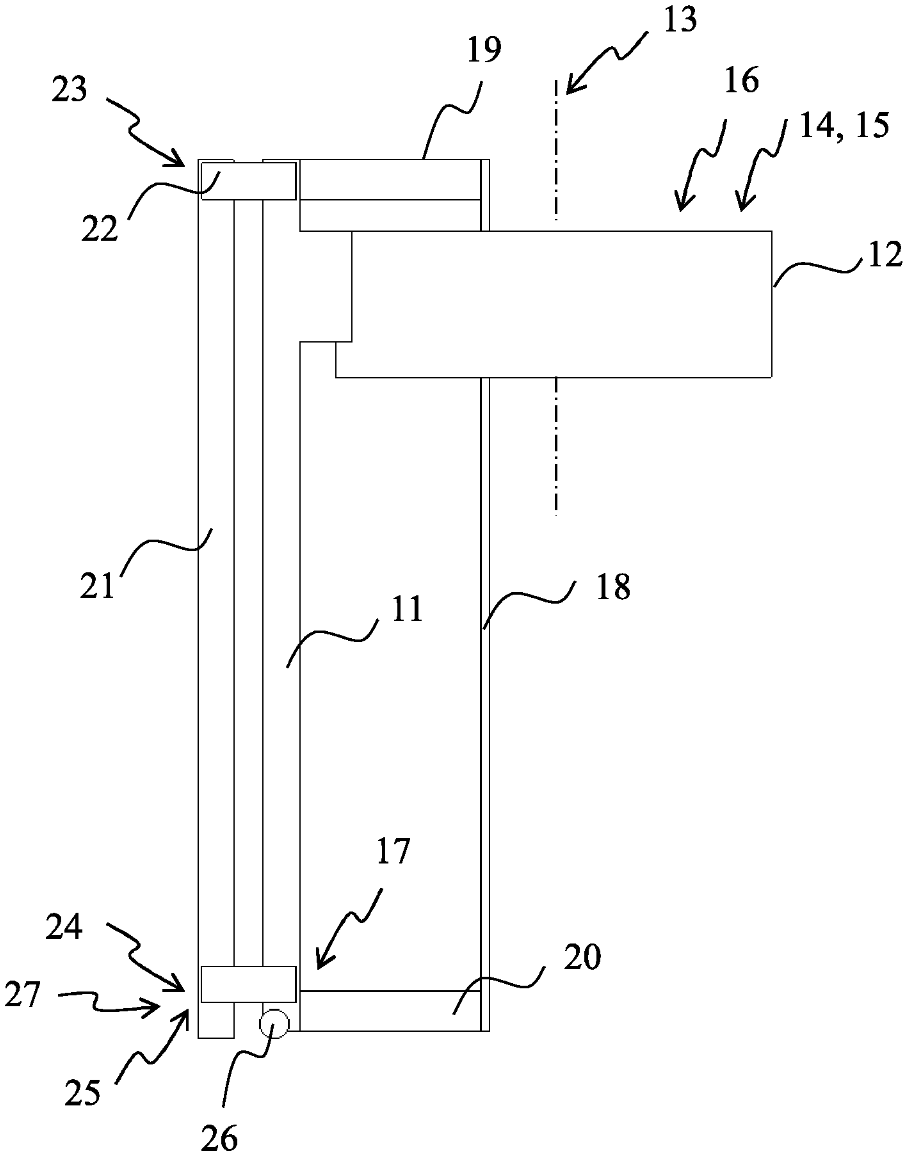
FIG. 5 is a schematic general side view showing certain components of an embodiment, as an example, of one kind of apparatus in which a cabling structure of this disclosure can be implemented.

Turning to FIG. 5 which shows, as a schematic general side view, certain components of an embodiment, as an example, of an apparatus according to this disclosure in which, in addition to what can be referred to as a first elongated frame part 11 discussed above, there is a second elongated frame part 21 mechanically connected to the first elongated frame part 11 of essentially the same length as the first elongated frame part 11.

According to one aspect and still referring to FIG. 5, at the proximity of the first end of the first elongated frame parts 11, 12 is arranged an articulated connection construction 22 to mechanically connect the first and second elongated frame parts 11, 21, to allow for tilting of the first elongated frame part 11 about at least one tilt axis in relation to the second elongated frame part 21. The at least one tilt axis is orthogonal to both the abovementioned first and second directions in which the elongated frame part 11 and the support construction 12 extend. Or, in other words, the tilt axis may be an axis which is orthogonal to the direction in which the first and second elongated frame parts 11, 21 extend as well as to direction in which the support construction 12 for the X-ray imaging assembly 14, 15 extends—perpendicularly from the first longitudinally extending frame part 11.

In the embodiments shown in the FIGS. and discussed in more detail in this application, the at least one tilt axis is horizontal. This is not to be understood that the tilt axis needs to be horizontal.

According to another aspect, on the side of the second elongated frame part 21, a mounting structure 23 not directly visible in FIG. 5 is arranged in connection with the articulated connection construction 22. The mounting structure 23 is arranged movable along or alongside the second elongated frame part 21.

According to another aspect, for example, at the proximity of the second end of the second elongated frame part 21 is arranged a locking mechanism 24 configured to enable connecting and disconnecting the first and second elongated frame parts 11, 21. Particularly, a locking mechanism 24 may be arranged at the proximity of the second end of the first and second elongated frame parts 11, 21, the locking mechanism being configured to enable connecting together and disconnecting the first and second elongated frame parts 11, 21 at the proximity of the second ends of the first and second elongated frame parts 11, 21.

When the second elongated frame part 21 is mounted stable and the locking mechanism 24 is not connecting the first and second elongated frame parts 11, 21, the second end of the first elongated frame part 11 is free to move laterally while the articulated connection 22 between the frame parts 11, 21 allows for turning of the first elongated frame part 11 about the horizontal tilt axis at the proximity of the first end of the first elongated frame part 11. In case of a vertical starting position, such movably arranged mounting structure as discussed above allows for descending and ascending of the first end of the first elongated frame part 11.

Figure 6:
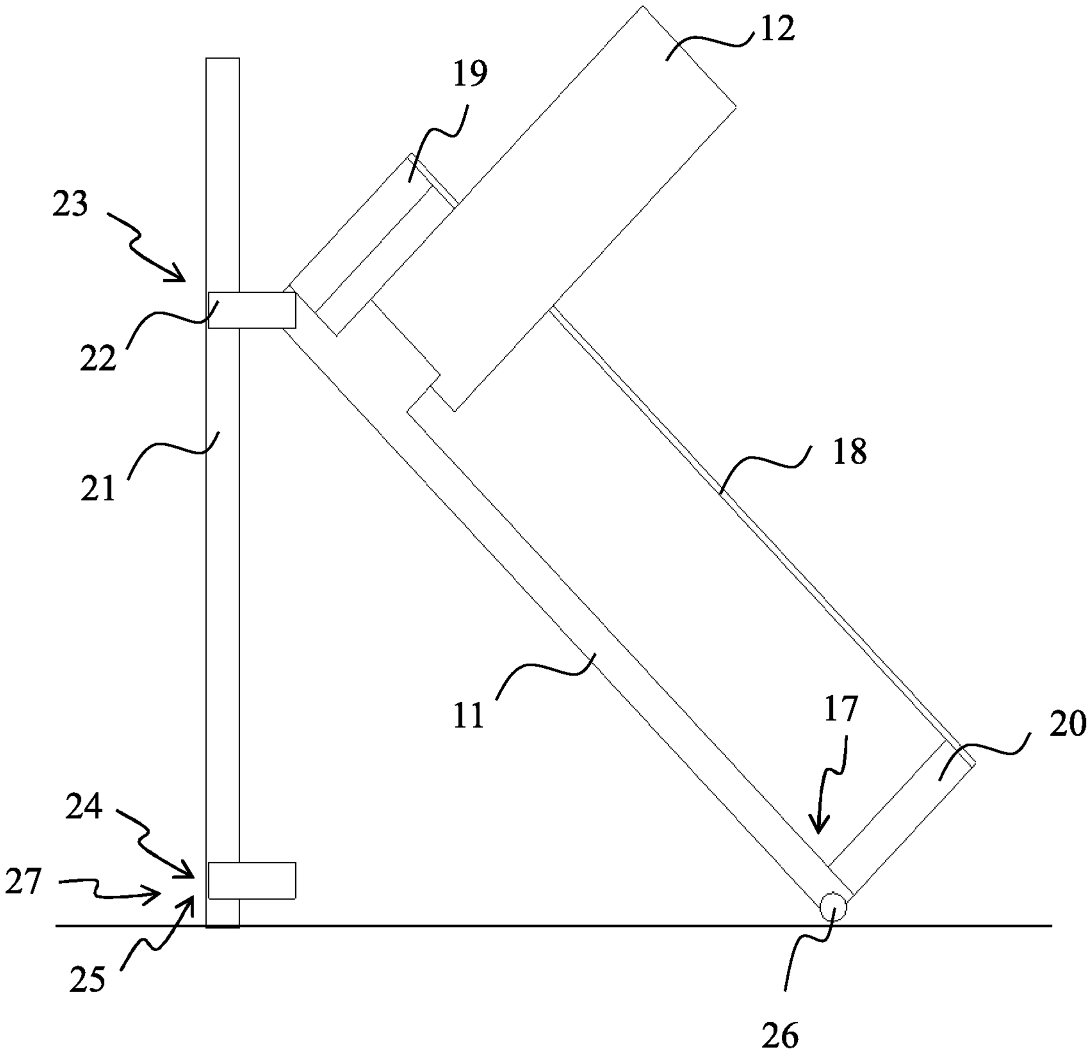
FIG. 6 is a schematic general side view of the apparatus of FIG. 5 showing certain components of the construction as driven at an inclined position.

FIG. 6 shows the apparatus according to FIG. 5 at a stage where the first end of the first elongated frame part 11 has moved downwards and the second end of the first elongated frame part 11 has moved horizontally on a surface. The apparatus may be configured to allow for descending of the first end of the first elongated frame part 11 all the way to the proximity of the second end of the second elongated frame part 21.

According to yet another aspect, not directly visible in FIGS. 5 and 6, in functional connection with the second elongated frame part 21 may be arranged a driving mechanism 27 to drive the mounting structure 23 along or alongside the second elongated frame part 21. When being in mechanical connection with the first elongated frame part 11, at the proximity of the first end of it, the driving mechanism 27 can move the first end of the first elongated frame part 11 in a direction in which the second elongated frame part 21 extends.

The driving mechanism 27 to drive the mounting structure 23 may be a construction similar with the driving mechanism 17 driving the support construction 12 of the X-ray imaging means 14, 15 along or alongside the first elongated frame part 11.

According to one aspect, the driving mechanism 27 to drive the mounting structure 23 comprises a chain drive.

To describe some of the features discussed above in other words, in an embodiment in mechanical connection with the articulated connection construction 22, on the side of the second elongated frame part 21, is arranged a mounting structure 23 which is arranged movable along or alongside the second elongated frame part 21, such construction thereby providing a degree of freedom of movement along or alongside the second frame part 21 for the articulated connection construction 23 and for the first end of the first elongated frame part 11 mechanically connected to the articulated connection construction 23.

In an embodiment, the mounting structure 23 is arranged movable along or alongside the second elongated frame part 21 at least essentially a distance corresponding to the length of the first elongated frame part 11, and the articulated connection construction 22 is arranged to allow for tilting of the first elongated frame part 11 between orientations at which the first and second elongated frame parts 11, 21 extend essentially in parallel and at which the first and second elongated frame parts 11, 21 extend essential orthogonally.

According to yet another aspect, the locking mechanism 24 comprises a displacement mechanism 25 which is not directly visible in FIGS. discussed so far to move the second end of the first elongated frame part 11 a distance away from the second elongated frame part 21 when the locking mechanism 24 disconnects the first and second elongated frame parts 11, 21.

According to one aspect not shown in detail in the FIGS. discussed so far, the locking mechanism 24 comprises a motor driven arrangement with mating components on the side of a motorized structure and the first elongated frame part 11, respectively.

The locking mechanism 24 may further comprise a guiding construction configured to guide the second end of the first elongated frame part 11 straight on the locking mechanism 24 when the second end of the first elongated frame part 11 is moving towards the locking mechanism 24. Or, to put it in other words, when the second end of the first elongated frame part 11 moves towards and approaches the second end of the second elongated frame part 21.

According to yet another aspect and, as shown as an example in FIGS. 4 and 5, the first elongated frame part 11 comprises at the proximity of its second end at least one wheel or roller 26.

According to another aspect, instead of the wheel or roller, a structure designed to slide on a surface may be arranged at the second end of the first elongated frame part 11.

A more detailed embodiment concerning some of the features discussed above is presented in FIG. 6, which overall shows the second ends of the first and second elongated frame parts 11, 21 yet wherein the very end of the second end of the first elongated frame parts 11 is cut, partly completely cut and partly just one wall being cut so that what could be called a back wall 11' is still visible.

Figure 7:
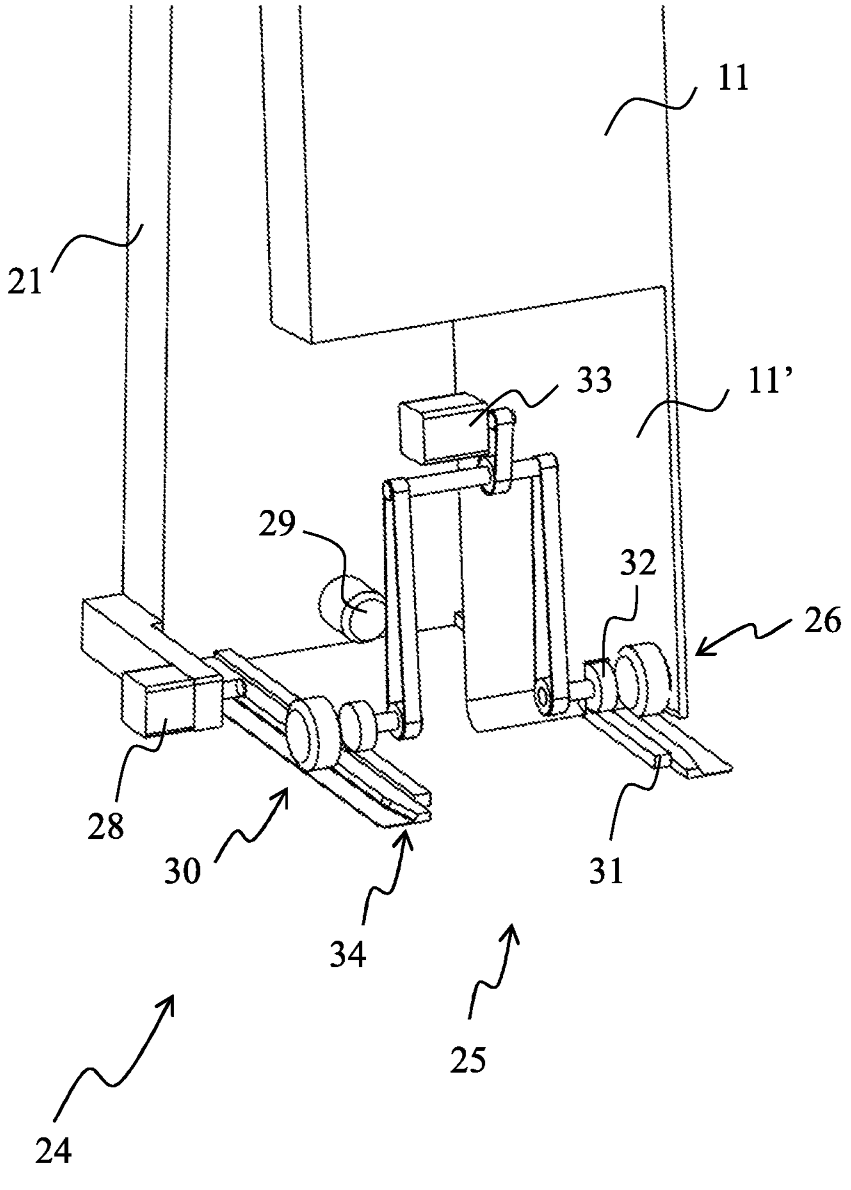
FIG. 7 shows components of an arrangement that can be used as a displacement and locking mechanism relating to the functionality of the apparatus as shown in FIGS. 5 and 6.

The embodiment shown in FIG. 7 includes a structure in which the displacement mechanism 25 comprises two toothed bars 31 mounted at the proximity of the second end of the second elongated frame part 21, to extent essentially orthogonally to the direction at which the second elongated frame part 21 extends, and two toothed wheels 32 mounted at the proximity of the second end of the first elongated frame part 11. The toothed wheels 32 are configured compatible with the toothed bars 31. While two toothed bars and wheels are shown, the number of those could be just one, or more than two.

The embodiment shown in FIG. 7 further includes the displacement mechanism 25 comprising a displacing motor 33 arranged in functional connection with toothed wheels 32.

According to one embodiment, to operate the displacement mechanism 25, the control system of the apparatus may be configured to, when the first and second elongated frame parts 11, 21 extend essentially in parallel and as a response to a control signal to alter the mutual orientation of the first and second elongated frame parts 11, 21, first operate the displacement mechanism 25 to move the second end of the first elongated frame part 11 a distance away from the second end of the second elongated frame part 21 and, second, operate said third driving mechanism 27 to drive the mounting structure 23 along or alongside the second elongated frame part 21 towards the second end of the second elongated frame part 21, so as to move the second end of the first elongated frame part 11 a further distance away from the second end of the second elongated frame part 21.

The locking mechanism 24 shown in FIG. 7 further comprises a sensing element 29 configured to detect when the second end of the first elongated frame part 11, when moving towards the second end of the second elongated frame part 21, has reached a predefined locking position.

The locking mechanism 24 shown in FIG. 7 further comprises a locking actuator 28 and the control system of the apparatus may be configured to, as a response to a control signal from the sensing element 29 that the second end of the first elongated frame part 11 when moving towards the second end of the second elongated frame part 21 has reached a predefined locking position, send a control signal to the locking actuator 28 to lock the second end of the first elongated frame part 11 at said predefined locking position.

The guiding construction according the embodiment of FIG. 7 comprises two guide rails 30 mounted from their first end at the proximity of the second end of the second elongated frame part 21 and extending essentially orthogonally to the direction at which the second elongated frame part 21 extends, to form two guide passages. While two guide rails 30 are shown in FIG. 7, the number of rails could be something else as well—yet, using just one rail it may be difficult to form a passage truly having a guiding function.

While shown in FIG. 7 is the first elongated frame part 11 to comprise at the proximity of its second end two wheels, or rollers 26, at a first distance from each other, and the guiding construction to comprise two guide rails 30 to form two guide passages essentially at the same first distance from each other, the guide rails 30 further comprise at their second ends a beveling so as to make a distance between the guide passages smaller at that end of the passages than the first distance. Such construction aids in guiding the second end of the first elongated frame part 11 to find a designed passage to move towards the second elongated frame part 21.

Figure 8:
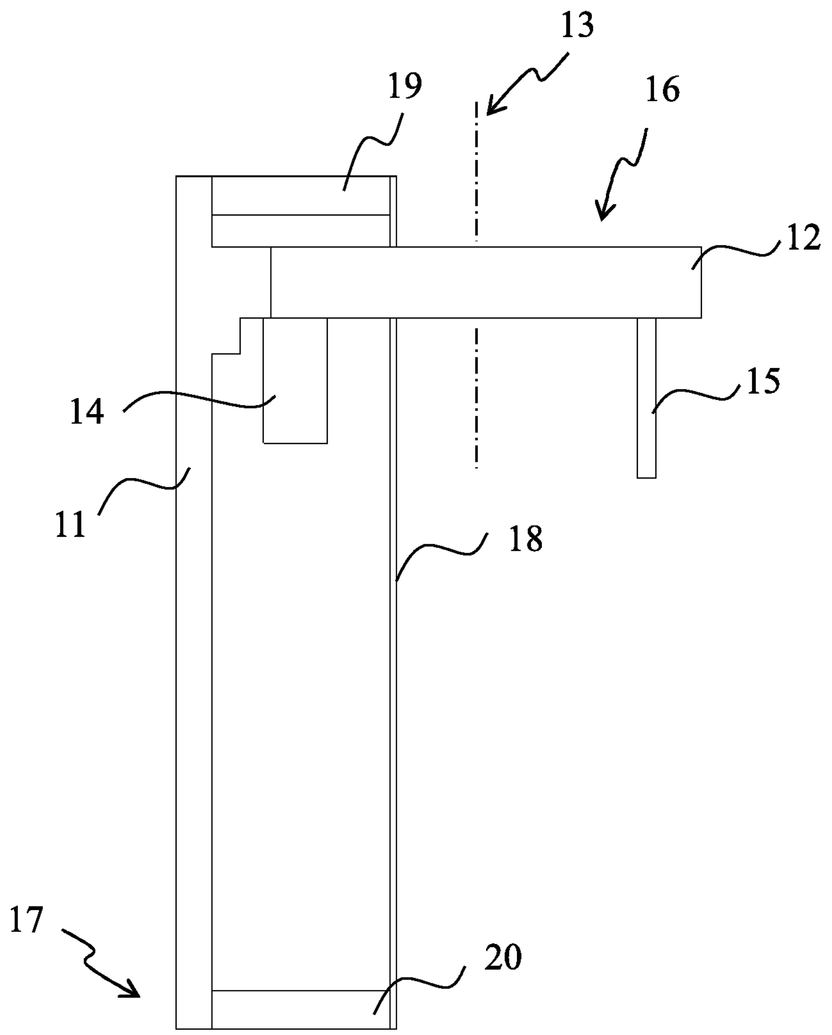
FIG. 8 is a schematic general side view showing certain components of another embodiment, as an example, of one kind of apparatus in which a cabling structure of this disclosure can be implemented.

According to one aspect, for example and as shown in FIG. 8, support construction 12 for the imaging means 14, 15 in a form of a gantry basically does not completely encircle the imaging means 14, 15 but functions primarily or solely as a support structure for holding the imaging means 14, 15, and structures arranged to the gantry to drive the imaging means 14, 15 about an axis. This kind of solution enables realizing the gantry as less heavy and as providing better access to the volume between the imaging means 14, 15, both physically and considering an area from where one may have a clear line of sight at that volume.

Figure 9:
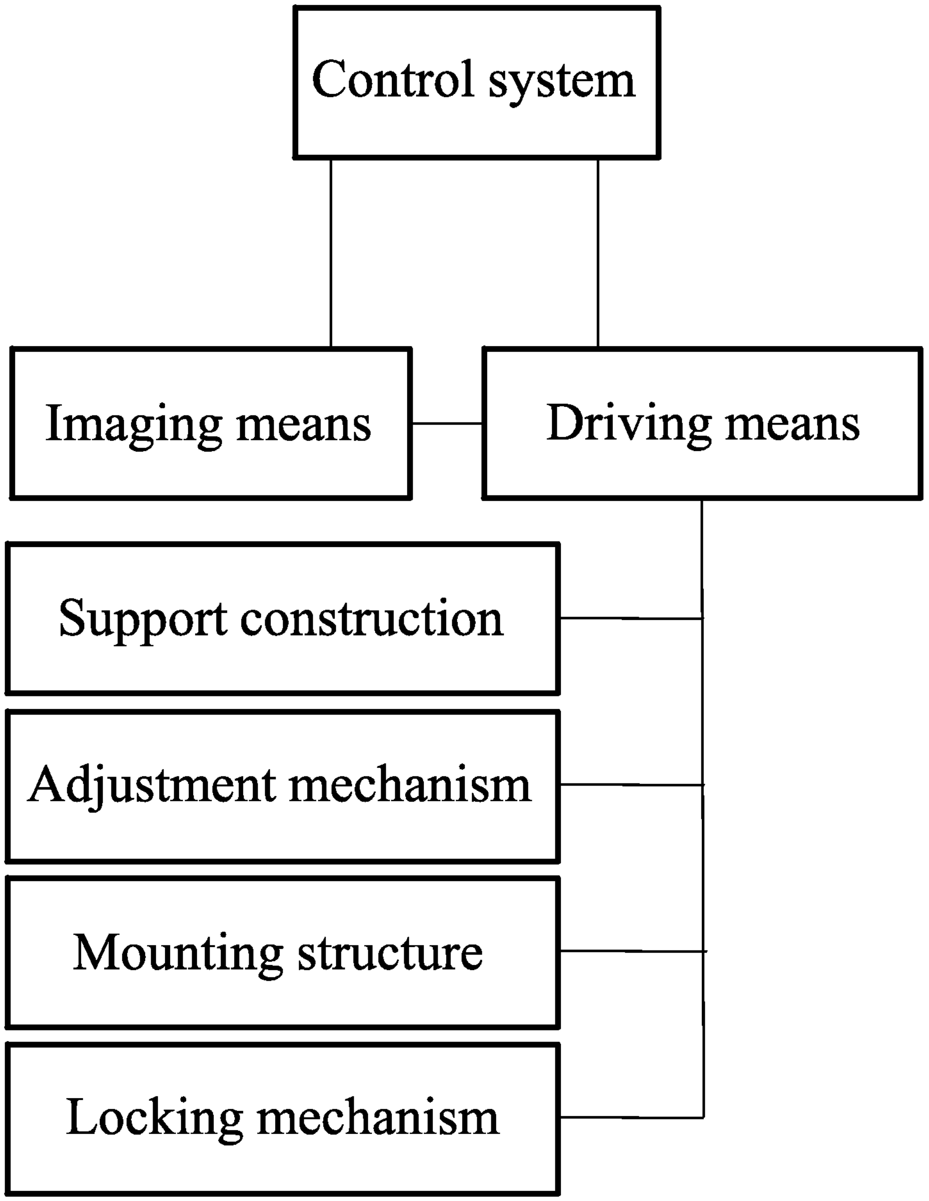
FIG. 9 is a block diagram showing an example of components of an embodiment of an apparatus according this disclosure which a control system of the apparatus may be configured to control.

FIG. 9 shows as a block diagram an example of features of a control system applicable for use in an apparatus according to this disclosure. In various embodiments, not all those features are necessarily present. The control system according to FIG. 9 is configured to enable controlling, first of all, operation of the X-ray source and the image detector. Components controlling operation of the X-ray source and the image detector can include components physically arranged to the X-ray source and/or the image detector and/or elsewhere in the apparatus.

The control system of FIG. 9 further controls driving means of the apparatus, which may include one or more of those moving the imaging means, their support construction and the adjustment mechanism of the patient support. The control system may also control e.g. driving of the mounting structure as discussed above. Further, in case of the apparatus comprising a motorized locking mechanism to connect and disconnect the first and second elongated frame parts, the control system may also control driving means of the locking mechanism, like the displacing motor and the locking actuator discussed above. Overall, the control system may be arranged to control all the above-discussed operations or any portion thereof. Inputs to the control system may be provided by the remote control. The structures and functionalities discussed above offer various possibilities for positioning and imaging a patient.

Overall when considering what has been discussed above relating to embodiments like the ones shown in FIGS. 3 and 4, such can be characterized, as an example, as including a cabling 124 running into and inside the first support construction 12 and further to at least either of the X-ray imaging means 14, 15, the cabling 124 conveying at least either of electric power and data;

an inner cabling support structure 122 having an outer surface and an inner surface and comprising a virtual central axis 13 within the inner surface;

a roller cylinder assembly 123' arranged rotatable outside the inner cabling support structure 122 and comprising at least a first roller cylinder 123, the at least first roller cylinder 123 being rotatable about itself;

an outer cabling support structure 121 arranged outside the roller cylinder assembly 123';

a first entry location 1211 and a first exit location 1221 for a first section 124' of the cabling 124, wherein either one of the first entry location 1211 and the first exit location 1221 is arranged to the inner cabling support structure 122 and the other one to the outer cabling support structure 121;

a first cable fixing structure 1212 arranged to or in connection with the outer cabling support structure 121, optionally at or at the proximity of the entry or exit location 1211, 1221 of the outer cabling support structure 121, to fix the cabling 124 immovable in relation thereto;

a second cable fixing structure 1222 arranged to or in connection with the inner cabling support structure 122, optionally at or at the proximity of the entry or exit location 1211, 1221 of the inner cabling support structure 122, to fix the cabling 124 immovable in relation thereto;

a first driving mechanism 16 in form of or comprising a rotation drive construction 160;

wherein either of i) the inner cabling support structure 122 and ii) the outer cabling support structure 121 is arranged to the first support construction 12 as rotatable and the X-ray imaging means 14, 15 are mounted to that rotatable cabling support structure 121, 122, and wherein the rotation drive construction 160 is configured to generate rotating of, in a first direction, either of i) said rotatable cabling support structure 121, 122 or ii) the roller cylinder assembly 123', and wherein considering a mutual rotational position of the inner and outer cabling support structure 122, 121 and a related shortest possible distance from the first entry location 1211 to the first exit location 1221, a length of a section of the cabling 124 extending between the first and second cable fixing structures 1212, 1222 is at least as long or longer than what is needed for the first section of the cabling 124' to extend said shortest possible distance from the first entry location 1211 to the first exit location 1221 and, further, to be able to form in more than one mutual rotational position of said cabling support structures 121, 122 and the rotatable roller cylinder assembly 123' a partial loop around said first roller cylinder 123.

According to one aspect then, for example, when considering instantaneous rotation in said first direction and the first roller cylinder 123, the first roller cylinder 123 has a front side pointing to the direction of movement in the first direction and a back side opposite to the front side, and wherein in case of the rotation drive construction being configured to generate rotating in the first direction of said rotatable cabling support structure 121, 122, the first section 124 of the cabling 124' is assembled such that it is able to make said partial loop around the first roller cylinder 123 from the back side thereof, the first section 124 of the cabling 124' thus pulling the roller cylinder assembly 123' while also causing rotating of the first roller cylinder 123, or in case of the rotation drive construction being configured to generate rotating in the first direction of said rotatable roller cylinder assembly 123', the first section of the cabling 123 is assembled such that it is able to make said partial loop around the first roller cylinder 123 from the front side thereof, the first section 124 of the cabling 124' thus pulling the rotatable cabling support structure 121, 122 while also causing rotating of the first roller cylinder 123. According to another aspect, for example, the length of the first section 124' of the cabling 124 extending between the first entry location 1211 and the first exit location 1221 is long enough to enable the first section 124' of the cabling 124 to form said partial loop and to extend on a virtual curved surface locating between the inner and outer cabling support structures 121, 122 a distance corresponding to an angular displacement on said virtual curved surface of tens of degrees, or up to or close to 360 degrees.

The inner cabling support structure 122 may be circular and the roller cylinder assembly 123', the inner cabling support structure 122 and thickness of the first section of the cabling 124 so dimensioned that the first section of the cabling 124, when in contact with said at least first roller cylinder 123 of the roller cylinder assembly 123', is also in contact with said outer surface of the inner cabling support structure 122.

According to one aspect, the rotation drive construction 160 is configured to generate rotating of the inner cabling support structure 122.

According to another aspect, at least the first roller cylinder 123 comprises a cylindrical outer surface and, at or at a proximity of both the edges thereof, a protruding edge or protruding elements.

According to one aspect, the outer cabling support structure 121 has a circular inner surface and the roller cylinder assembly 123' comprises a set of guide wheels 125 configured to support the roller cylinder assembly 123' by the guide wheels 125 which are arranged to be in contact with the circular inner surface of the outer cabling support structure 121, and that optionally or alternatively a similar or similarly functioning structure is arranged to the roller cylinder assembly 123' to provide support to the roller cylinder assembly 123' from a circular outer surface of the inner cabling support structure 122.

The cabling 124 within the first section 124' of cabling may be or include a flat cable.

According to one aspect, the roller cylinder assembly 123' comprises at least seven roller cylinders 123, such as ten roller cylinder 123, and/or optionally said first roller cylinder 123 has larger physical dimensions than those of some or the rest of the other roller cylinders 123.

According to another aspect, there is a second entry location 1211 and a second exit location 1221, the second entry location 1211 comprising a third cable fixing structure 1212 arranged to the outer cabling support structure 121 and the second exit location 1221 comprising a fourth cable fixing structure 1222 arranged to the inner cabling support structure 122, wherein an elongated flexible component 124" is arranged to extend between the second entry location 1211 to the second exit location 1221 and being attached to the third and fourth cable fixing structures 1212, 1222, and wherein, optionally, concerning at least one of i) the elongated flexible component 124", ii) the second entry and exit locations, 1211, 1221, iii) the third and fourth cable fixing structure 1212, 1222:

the elongated flexible component 124" constitutes a second section 124" of the cabling 124, the second entry location 1211 is the same as the first entry location 1211, the second exit location 1221 is the same as the first exit location 1221, the third cable fixing structure 1212 is part of or the same as the first cable fixing structure 1212, and the fourth cable fixing structure 1222 is a part of or the same as the second cable fixing structure 1222.

According to one aspect, concerning that one of the structures i) the cabling support structure 121, 122 and ii) the roller cylinder assembly 123' the rotation drive construction 160 is configured to rotate in the first direction, the rotation drive construction 160 is configured to further generate rotating of that one of said structures in a direction opposite to the first direction, and that considering more than one mutual rotational position of the inner and outer cabling support structure 122, 121 and a related shortest possible distance from the second entry location 1211 to the second exit location 1221, a length of a section of the elongated flexible component 124" extending between the third and fourth cable fixing structures 1212, 1222 is at least as long or longer than what is needed for the elongated flexible component 124" to extend said shortest possible distance from the second entry location 1211 to the second exit location 1221 and, further, to be able to form in more than one mutual rotational position of said cabling support structures 121, 122 and the rotatable roller cylinder assembly 123', a partial loop around a second roller cylinder 123 included in the roller cylinder assembly 123', wherein the second roller cylinder 123 is optionally the same as the first roller cylinder 123.

In an embodiment, when considering instantaneous rotation in said first direction and the second roller cylinder 123, the second roller cylinder 123 has a front side pointing to the direction of movement in the first direction and back side opposite to the front side, and wherein in case of the rotation drive construction being configured to generate rotating in the direction opposite to the first direction of said rotatable cabling support structure 121, 122, the elongated flexible component 124" is assembled such that it is able to make said partial loop around the second roller cylinder 123 from the front side thereof, the elongated flexible component 124" thus pulling the roller cylinder assembly 123' while also causing rotating of the second roller cylinder 123, and in case of the rotation drive construction being configured to generate rotating in the direction opposite to the first direction of said rotatable roller cylinder assembly 123', the elongated flexible component 124" is assembled such that it is able to make said partial loop around the second roller cylinder 123 from the back side thereof, the elongated flexible component 124" thus pulling the rotatable cabling support structure 121, 122 while also causing rotating of the second roller cylinder 123.

According to one aspect, the length of the elongated flexible component 124", or of the second section 124" of the cabling 124 extending between the second entry location 1211 and the second first exit location 1221, is long enough to enable the elongated flexible component 124" or the second section 124" of the cabling 124 to form said partial loop and to extend on a virtual curved surface locating between the inner and outer cabling support structures 121, 122 a distance corresponding to an angular displacement on said virtual curved surface of tens of degrees, or up to or close to 360 degrees.

According to another aspect, the inner cabling support structure 122 is circular, and the roller cylinder assembly 123', the inner cabling support structure 122 and thickness of the elongated flexible component 124", or of the second section 124" of the cabling 124 are so dimensioned that the elongated flexible component 124" or the second section 124" of the cabling 124, when in contact with said second roller cylinder 123 of the roller cylinder assembly 123', is also in contact with said outer surface of the inner cabling support structure 122.

The second roller cylinder 123 may be the same as the first roller cylinder 123 and, the elongated flexible component 124" and the second section 124" of the cabling 124 be arranged to form their partial loops around the first roller cylinder 123. These partial loops may be located on the first roller cylinder 123 at a lateral distance from each other.

According to one aspect, the elongated flexible component 124" is the second section 124" of the cabling 124, and one of the i) first section 124' and ii) second section 124" of the cabling 124 is a power cable, optionally a flat cable, and the other one is a data cable, optionally a flat cable.

The invention claimed is:

1. A dental or medical X-ray imaging apparatus, comprising:

a first elongated frame part;

a first support construction extending from the first elongated frame part;

an X-ray source and an image detector, which together form an X-ray imaging means, mounted to the first support construction;

a cabling running into and inside the first support construction and further to at least either of the X-ray imaging means, the cabling conveying at least either of electric power and data;

a control system;

characterized by the first support construction comprising:

an inner cabling support structure having an outer surface and an inner surface and comprising a virtual central axis within the inner surface;

a roller cylinder assembly arranged rotatable outside the inner cabling support structure and comprising at least a first roller cylinder, the at least first roller cylinder being rotatable about itself;

an outer cabling support structure arranged outside the roller cylinder assembly;

a first entry location and a first exit location for a first section of the cabling, wherein either one of the first entry location and the first exit location is arranged to the inner cabling support structure and the other one to the outer cabling support structure;

a first cable fixing structure arranged to or in connection with the outer cabling support structure, optionally at or at the proximity of the entry or exit location of the outer cabling support structure, to fix the cabling immovable in relation thereto;

a second cable fixing structure arranged to or in connection with the inner cabling support structure, optionally at or at the proximity of the entry or exit location of the inner cabling support structure, to fix the cabling immovable in relation thereto;

a first driving mechanism in form of or comprising a rotation drive construction;

wherein either of i) the inner cabling support structure and ii) the outer cabling support structure is arranged to the first support construction as rotatable and the X-ray imaging means are mounted to that rotatable cabling support structure, and wherein the rotation drive construction is configured to generate rotating of, in a first direction, either of i) said rotatable cabling support structure or ii) the roller cylinder assembly, and wherein considering a mutual rotational position of the inner and outer cabling support structure and a related shortest possible distance from the first entry location to the first exit location, a length of a section of the cabling extending be-tween the first and second cable fixing structures is at least as long or longer than what is needed for the first section of the cabling to extend said shortest possible distance from the first entry location to the first exit location and, further, to be able to form in more than one mutual rotational position of said cabling support structures and the rotatable roller cylinder assembly a partial loop around said first roller cylinder.

2. The apparatus according to claim 1, characterized in that when considering instantaneous rotation in said first direction and the first roller cylinder, the first roller cylinder has a front side pointing to the direction of movement in the first direction and a back side opposite to the front side, and wherein in case of the rotation drive construction being configured to generate rotating in the first direction of said rotatable cabling support structure, the first section of the cabling is assembled such that it is able to make said partial loop around the first roller cylinder from the back side thereof, the first section of the cabling thus pulling the roller cylinder assembly while also causing rotating of the first roller cylinder, or in case of the rotation drive construction being configured to generate rotating in the first direction of said rotatable roller cylinder assembly, the first section of the cabling is assembled such that it is able to make said partial loop around the first roller cylinder from the front side thereof, the first section of the cabling thus pulling the rotatable cabling support structure while also causing rotating of the first roller cylinder.

3. The apparatus according to claim 1, characterized in that the length of the first section of the cabling extending between the first entry location and the first exit location is long enough to enable the first section of the cabling to form said partial loop and to extend on a virtual curved surface locating between the inner and outer cabling support structures a distance corresponding to an angular displacement on said virtual curved surface of up to 360 degrees.

4. The apparatus according to claim 1, characterized in that the inner cabling support structure is circular, and the roller cylinder assembly, the inner cabling support structure and thickness of the first section of the cabling are so dimensioned that the first section of the cabling, when in contact with said at least first roller cylinder of the roller cylinder assembly, is also in contact with said outer surface of the inner cabling support structure.

5. The apparatus according to claim 1, characterized in that the rotation drive construction is configured to generate rotating of the inner cabling support structure.

6. The apparatus according to claim 1, characterized in that at least the first roller cylinder comprises a cylindrical outer surface and, at or at a proximity of both the edges thereof, a protruding edge or protruding elements.

7. The apparatus according to claim 1, characterized in that the outer cabling support structure has a circular inner surface and the roller cylinder assembly comprises a set of guide wheels configured to support the roller cylinder assembly by the guide wheels which are arranged to be in contact with the circular inner surface of the outer cabling support structure.

8. The apparatus according to claim 1, characterized in that the cabling within said first section of cabling is or includes a flat cable.

9. The apparatus according to claim 1, characterized in that the apparatus comprises a second elongated frame part comprising a first end and a second end of essentially the same length as the first elongated frame part, wherein at the proximity of the first end of the first elongated frame part is arranged an articulated connection construction to mechanically connect the first and second elongated frame parts, to allow for tilting of the first elongated frame part about at least one tilt axis in relation to the second elongated frame part, the at least one tilt axis being orthogonal to both said first and second directions.

10. The apparatus according to claim 9, characterized in that in mechanical connection with the articulated connection construction, on the side of the second elongated frame part, is arranged a mounting structure which is arranged movable along or alongside the second elongated frame part, thereby providing for the articulated connection construction and for the first end of the first elongated frame part mechanically connected to the articulated connection construction a degree of freedom of movement along or alongside the second elongated frame part.

11. The apparatus according to claim 10, characterized in that the mounting structure is arranged movable along or alongside the second elongated frame part at least essentially a distance corresponding to the length of the first elongated frame part, and the articulated connection construction is arranged to allow for tilting of the first elongated frame part between orientations at which the first and second elongated frame parts extend essentially in parallel and at which the first and second elongated frame parts extend essential orthogonally.

12. The apparatus according to claim 1, characterized in that the apparatus comprises a patient support which is a structure mechanically connected to the first elongated frame part and extending substantially in parallel with the first elongated frame part and is essentially of the same length as the first elongated frame part.

13. A dental or medical X-ray imaging apparatus, comprising:
- a first elongated frame part;
- a first support construction extending from the first elongated frame part;
- an X-ray source and an image detector, which together form an X-ray imaging means, mounted to the first support construction;
- a cabling running into and inside the first support construction and further to at least either of the X-ray imaging means, the cabling conveying at least either of electric power and data;
- a control system;

characterized by a combination of constructions:

the first support construction comprises:
- an inner cabling support structure having an outer surface and an inner surface and comprising a virtual central axis within the inner surface;
  - a roller cylinder assembly arranged rotatable outside the inner cabling support structure and comprising at least a first roller cylinder, the at least first roller cylinder being rotatable about itself;
- an outer cabling support structure arranged outside the roller cylinder assembly;
- a first entry location and a first exit location for a first section of the cabling, wherein either one of the first entry location and the first exit location is arranged to the inner cabling support structure and the other one to the outer cabling support structure;
- a first cable fixing structure arranged to or in connection with the outer cabling support structure, optionally at or at the proximity of the entry or exit location of the outer cabling support structure, to fix the cabling immovable in relation thereto;
- a second cable fixing structure arranged to or in connection with the inner cabling support structure, optionally at or at the proximity of the entry or exit location of the inner cabling support structure, to fix the cabling immovable in relation thereto;
- a first driving mechanism in form of or comprising a rotation drive construction;
- wherein either of i) the inner cabling support structure and ii) the outer cabling support structure is arranged to the first support construction as rotatable and the X-ray imaging means are mounted to that rotatable cabling support structure, and wherein
- the rotation drive construction is configured to generate rotating of, in a first direction, either of i) said rotatable cabling support structure or ii) the roller cylinder assembly, and wherein
- considering a mutual rotational position of the inner and outer cabling support structure and a related shortest possible distance from the first entry location to the first exit location, a length of a section of the cabling extending between the first and second cable fixing structures is at least as long or longer than what is needed for the first section of the cabling to extend said shortest possible distance from the first entry location to the first exit location and, further, to be able to form in more than one mutual rotational position of said cabling support structures and the rotatable roller cylinder assembly a partial loop around said first roller cylinder;
- a second entry location and a second exit location, the second entry location comprising a third cable fixing structure arranged to the outer cabling support structure and the second exit location comprising a fourth cable fixing structure arranged to the inner cabling support structure,
- wherein an elongated flexible component is arranged to extend between the second entry location to the second exit location and being attached to the third and fourth cable fixing structures,
- and wherein, optionally, concerning at least one of i) the elongated flexible component, ii) the second entry and exit locations, iii) the third and fourth cable fixing structure:

the elongated flexible component constitutes a second section of the cabling, the second entry location is the same as the first entry location, the second exit location is the same as the first exit location, the third cable fixing structure is part of or the same as the first cable fixing structure, and the fourth cable fixing structure is a part of or the same as the second cable fixing structure; and wherein the outer cabling support structure has a circular inner surface and the roller cylinder assembly comprises a set of guide wheels configured to support the roller cylinder assembly by the guide wheels which are arranged to be in contact with the circular inner surface of the outer cabling support structure, and that optionally or alternatively a similar or similarly functioning structure is arranged to the roller cylinder assembly to provide support to the roller cylinder assembly from a circular outer surface of the inner cabling support structure.

14. The apparatus according to claim 13, characterized in that when considering instantaneous rotation in said first direction and the first roller cylinder, the first roller cylinder has a front side pointing to the direction of movement in the first direction and a back side opposite to the front side, and wherein in case of the rotation drive construction being configured to generate rotating in the first direction of said rotatable cabling support structure, the first section of the cabling is assembled such that it is able to make said partial loop around the first roller cylinder from the back side thereof, the first section of the cabling thus pulling the roller cylinder assembly while also causing rotating of the first roller cylinder, or in case of the rotation drive construction being configured to generate rotating in the first direction of said rotatable roller cylinder assembly, the first section of the cabling is assembled such that it is able to make said partial loop around the first roller cylinder from the front side thereof, the first section of the cabling thus pulling the rotatable cabling support structure while also causing rotating of the first roller cylinder.

15. The apparatus according to any of the claim 13, characterized in that the roller cylinder assembly comprises at least seven roller cylinders, such as ten roller cylinder, and/or optionally said first roller cylinder has larger physical dimensions than those of some or the rest of the other roller cylinders.

16. The apparatus according to any of the claim 13, characterized in that, concerning that one of the structures i) the cabling support structure and ii) the roller cylinder assembly the rotation drive construction is configured to rotate in the first direction, the rotation drive construction is configured to further generate rotating of that one of said structures in a direction opposite to the first direction, and that considering more than one mutual rotational position of the inner and outer cabling support structure and a related shortest possible distance from the second entry location to the second exit location, a length of a section of the elongated flexible component extending between the third and fourth cable fixing structures is at least as long or longer than what is needed for the elongated flexible component to extend said shortest possible distance from the second entry location to the second exit location and, further, to be able to form in more than one mutual rotational position of said cabling support structures and the rotatable roller cylinder assembly, a partial loop around a second roller cylinder included in the roller cylinder assembly, wherein the second roller cylinder is optionally the same as the first roller cylinder.

17. The apparatus according to claim 13, characterized in that when considering instantaneous rotation in said first direction and the second roller cylinder, the second roller cylinder has a front side pointing to the direction of movement in the first direction and back side opposite to the front side, and wherein in case of the rotation drive construction being configured to generate rotating in the direction opposite to the first direction of said rotatable cabling support structure, the elongated flexible component is assembled such that it is able to make said partial loop around the second roller cylinder from the front side thereof, the elongated flexible component thus pulling the roller cylinder assembly while also causing rotating of the second roller cylinder, and in case of the rotation drive construction being configured to generate rotating in the direction opposite to the first direction of said rotatable roller cylinder assembly, the elongated flexible component is assembled such that it is able to make said partial loop around the second roller cylinder from the back side thereof, the elongated flexible component thus pulling the rotatable cabling support structure while also causing rotating of the second roller cylinder.

18. The apparatus according to any of the claim 13, characterized in that the apparatus comprises a second elongated frame part comprising a first end and a second end of essentially the same length as the first elongated frame part, wherein at the proximity of the first end of the first elongated frame part is arranged an articulated connection construction to mechanically connect the first and second elongated frame parts to allow for tilting of the first elongated frame part about at least one tilt axis in relation to the second elongated frame part, the at least one tilt axis being orthogonal to both said first and second directions.

19. The apparatus according to claim 18, characterized in that in mechanical connection with the articulated connection construction, on the side of the second elongated frame part, is arranged a mounting structure which is arranged movable along or alongside the second elongated frame part, thereby providing for the articulated connection construction and for the first end of the first elongated frame part mechanically connected to the articulated connection construction a degree of freedom of movement along or alongside the second elongated frame part.

20. The apparatus according to claim 19, characterized in that the mounting structure is arranged movable along or alongside the second elongated frame part at least essentially a distance corresponding to the length of the first elongated frame part, and the articulated connection construction is arranged to allow for tilting of the first elongated frame part between orientations at which the first and second elongated frame parts extend essentially in parallel and at which the first and second elongated frame parts extend essential orthogonally.

21. The apparatus according to any of the claim 13, characterized in that the apparatus comprises a patient support which is a structure mechanically connected to the first elongated frame part and extending substantially in parallel with the first elongated frame part and is essentially of the same length as the first elongated frame part.

* * * * *